United States Patent
Goodman et al.

(10) Patent No.: US 9,974,952 B2
(45) Date of Patent: May 22, 2018

(54) SOUND PROCESSOR HOUSINGS, SOUND PROCESSORS AND IMPLANTABLE COCHLEAR STIMULATION SYSTEMS INCLUDING THE SAME

(75) Inventors: James P. Goodman, Valencia, CA (US); Adam Smith, Palm Desert, CA (US)

(73) Assignee: Advanced Bionics AG, Staefa (CH)

( * ) Notice: Subject to any disclaimer, the term of this patent is extended or adjusted under 35 U.S.C. 154(b) by 714 days.

(21) Appl. No.: 13/989,614

(22) PCT Filed: Nov. 19, 2011

(86) PCT No.: PCT/US2011/061563
§ 371 (c)(1),
(2), (4) Date: Jul. 27, 2013

(87) PCT Pub. No.: WO2012/082320
PCT Pub. Date: Jun. 21, 2012

(65) Prior Publication Data
US 2013/0296971 A1    Nov. 7, 2013

Related U.S. Application Data

(60) Provisional application No. 61/424,571, filed on Dec. 17, 2010.

(51) Int. Cl.
*A61N 1/36* (2006.01)
*H04R 25/00* (2006.01)
*A61N 1/375* (2006.01)

(52) U.S. Cl.
CPC ..... *A61N 1/36032* (2013.01); *A61N 1/36036* (2017.08); *A61N 1/375* (2013.01); *H04R 25/602* (2013.01)

(58) Field of Classification Search
CPC .. A61N 1/36; A61N 1/36032; A61N 1/36036; A61N 1/375; H04R 25/602
USPC ............................................. 607/36, 57, 137
See application file for complete search history.

(56) References Cited

U.S. PATENT DOCUMENTS

| | | | |
|---|---|---|---|
| 4,456,797 A | 6/1984 | Olsen | |
| 4,562,590 A | 12/1985 | DeLage | |
| 4,584,718 A | 4/1986 | Fuller | |
| 4,682,363 A | 7/1987 | Goldfarb et al. | |

(Continued)

FOREIGN PATENT DOCUMENTS

| | | |
|---|---|---|
| DE | 102007061313 A1 | 6/2009 |
| DE | 102009010376 A1 | 4/2010 |

(Continued)

OTHER PUBLICATIONS

PCT Search Report and Written Opinion dated Jul. 20, 2012 for PCT App. Ser. No. PCT/US2011/061563.

*Primary Examiner* — Christopher A Flory
(74) *Attorney, Agent, or Firm* — Henricks, Slavin & Holmes LLP

(57) ABSTRACT

Sound processor housings, sound processors and systems including sound processors are disclosed. The housings include a main portion with a power supply receptacle, a seal and power supply receptacle cover. The seal may include a deflectable portion and define a material-free region into which the deflectable portion deflects in response to the application of radial force by the power supply receptacle cover.

30 Claims, 9 Drawing Sheets

(56) References Cited

U.S. PATENT DOCUMENTS

| | | |
|---|---|---|
| 4,683,587 A | 7/1987 | Silverman |
| 4,727,599 A | 2/1988 | Rappaport et al. |
| 4,918,737 A | 4/1990 | Luethi |
| 5,294,988 A | 3/1994 | Wakabayashi et al. |
| 5,386,084 A | 1/1995 | Risko |
| 5,625,688 A | 4/1997 | Ford et al. |
| 5,704,803 A | 1/1998 | Oshima |
| 5,818,946 A | 10/1998 | Walter |
| 5,824,022 A | 10/1998 | Zilberman et al. |
| 5,853,005 A * | 12/1998 | Scanlon .................. 600/459 |
| 5,896,453 A | 4/1999 | Speaks |
| 6,041,128 A | 3/2000 | Narisawa et al. |
| 6,092,707 A | 7/2000 | Bowes, Jr. |
| 6,396,769 B1 | 5/2002 | Polany |
| 6,614,722 B2 | 9/2003 | Polany et al. |
| 6,831,988 B2 | 12/2004 | Vonlanthen |
| 6,954,405 B2 | 10/2005 | Polany et al. |
| 7,069,063 B2 | 6/2006 | Halkosaari et al. |
| D528,213 S | 9/2006 | Darley et al. |
| 7,158,376 B2 | 1/2007 | Richardson et al. |
| 7,194,101 B2 | 3/2007 | Vonlanthen |
| 7,248,712 B2 | 7/2007 | Gabathuler |
| 7,263,032 B2 | 8/2007 | Polany et al. |
| 7,312,984 B2 | 12/2007 | Richardson et al. |
| 7,394,911 B2 | 7/2008 | Joergensen et al. |
| 7,400,917 B2 | 7/2008 | Wood et al. |
| 7,440,579 B2 | 10/2008 | Vonlanthen |
| 7,486,992 B2 | 2/2009 | Pufulescu et al. |
| 7,503,790 B2 | 3/2009 | Bodmann et al. |
| 7,535,799 B2 | 5/2009 | Polany et al. |
| 8,259,159 B2 * | 9/2012 | Hu .................. 348/47 |
| 8,328,420 B2 * | 12/2012 | Abreu .................. 374/208 |
| 8,660,658 B2 * | 2/2014 | Walsh et al. .................. 607/57 |
| 2002/0119697 A1 | 8/2002 | Chan |
| 2002/0193136 A1 | 12/2002 | Halkosaari et al. |
| 2005/0181745 A1 | 8/2005 | Wood et al. |
| 2007/0106344 A1 | 5/2007 | Darley et al. |
| 2007/0270180 A1 | 11/2007 | Takagi |
| 2008/0165996 A1 | 7/2008 | Saito et al. |
| 2008/0273730 A1 | 11/2008 | Kral |
| 2008/0288022 A1 | 11/2008 | Van der Borght et al. |
| 2008/0298627 A1 | 12/2008 | Bonebright et al. |
| 2009/0008880 A1 | 1/2009 | Bodmann et al. |
| 2009/0017884 A1 | 1/2009 | Rotschild |
| 2009/0092270 A1 | 4/2009 | Ho et al. |
| 2009/0105605 A1 * | 4/2009 | Abreu .................. 600/549 |
| 2009/0239135 A1 | 9/2009 | Wang et al. |
| 2009/0306468 A1 * | 12/2009 | Tasker et al. .................. 600/41 |
| 2009/0325046 A1 | 12/2009 | Yang |
| 2010/0168670 A1 * | 7/2010 | Srisathapat et al. .......... 604/111 |
| 2010/0226519 A1 | 9/2010 | Spragge |
| 2011/0160652 A1 * | 6/2011 | Yodfat et al. .................. 604/66 |
| 2011/0287688 A1 | 11/2011 | Hang et al. .................. 446/153 |
| 2012/0041517 A1 * | 2/2012 | Walsh et al. .................. 607/57 |
| 2012/0092264 A1 * | 4/2012 | Cheney et al. .................. 345/169 |
| 2012/0095398 A1 * | 4/2012 | Fonacier et al. .............. 604/151 |
| 2012/0095399 A1 * | 4/2012 | Bazargan et al. .............. 604/151 |
| 2013/0003329 A1 * | 1/2013 | Petchey et al. ................ 361/760 |
| 2013/0296971 A1 * | 11/2013 | Goodman et al. .............. 607/57 |
| 2014/0052055 A1 * | 2/2014 | Yodfat et al. .................. 604/67 |
| 2014/0066851 A1 * | 3/2014 | Cheney et al. ................ 604/151 |

FOREIGN PATENT DOCUMENTS

| | | |
|---|---|---|
| EP | 1271898 A1 | 1/2003 |
| EP | 1271898 B1 | 4/2006 |
| GB | 2133133 A | 7/1984 |
| WO | WO 98/50281 A1 | 11/1998 |
| WO | WO 2005/062668 A1 | 7/2005 |
| WO | WO 2006/071210 A1 | 7/2006 |
| WO | WO 2007/102158 A2 | 9/2007 |
| WO | WO 2008/150642 A1 | 12/2008 |
| WO | WO 2009/063096 A2 | 5/2009 |

* cited by examiner

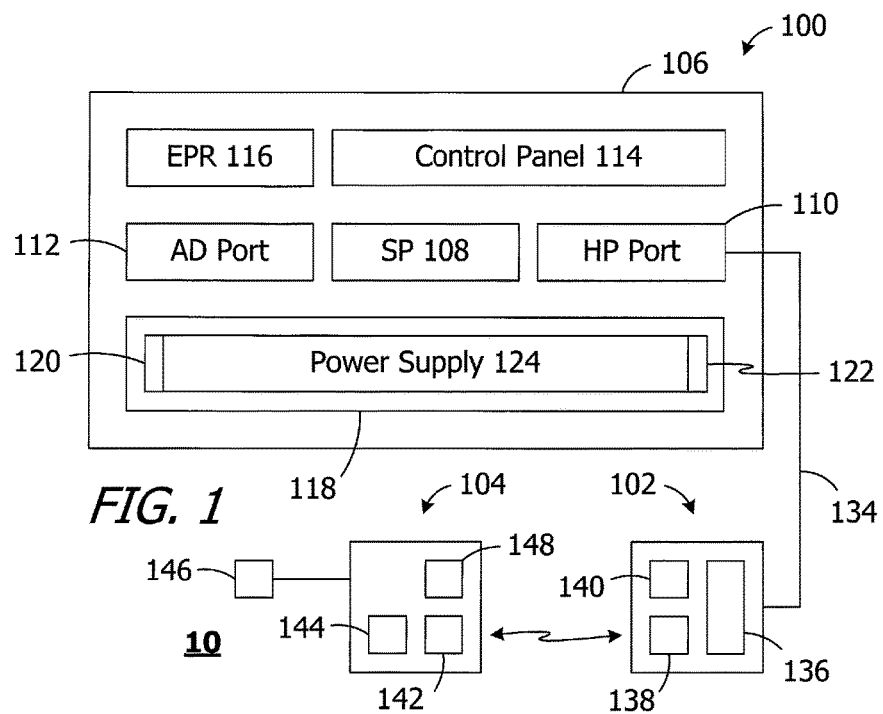
FIG. 1
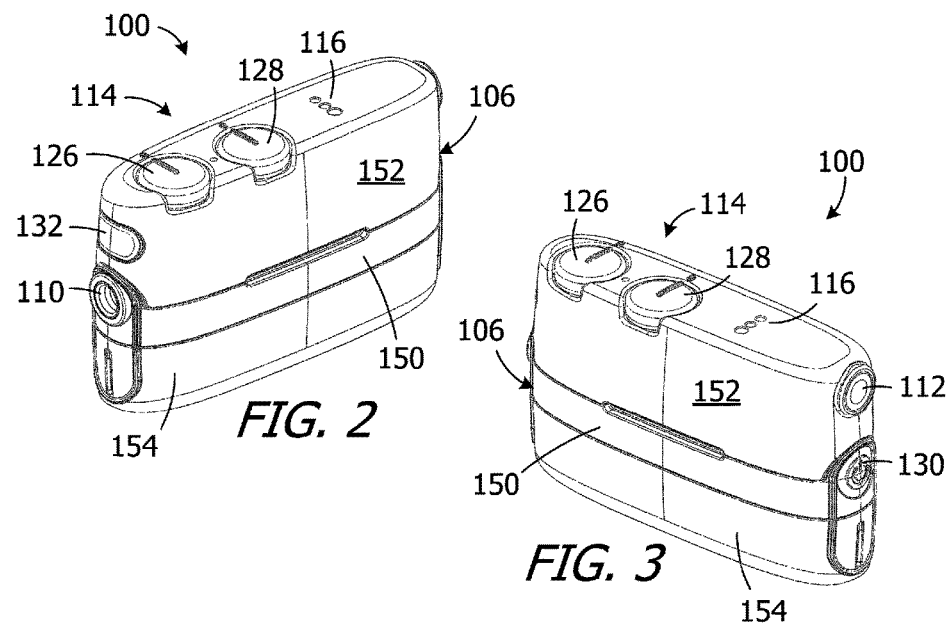
FIG. 2
FIG. 3

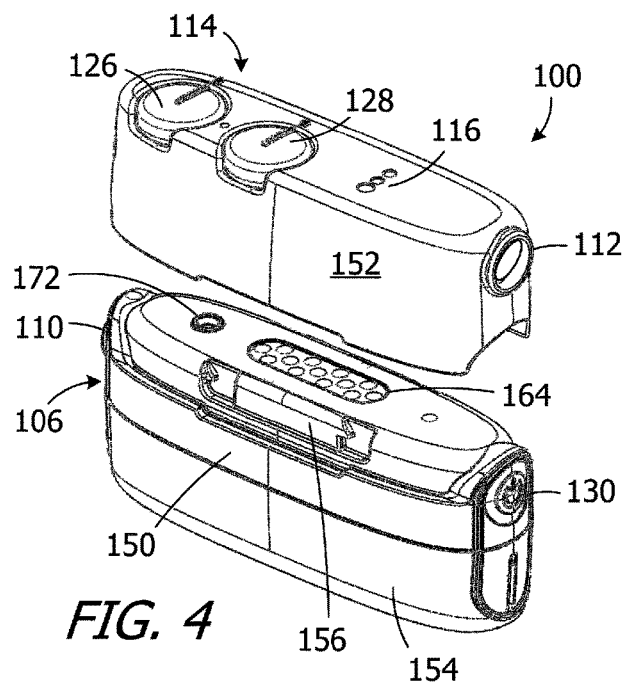
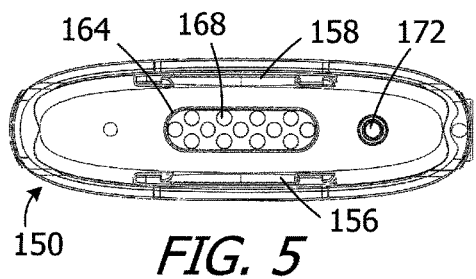 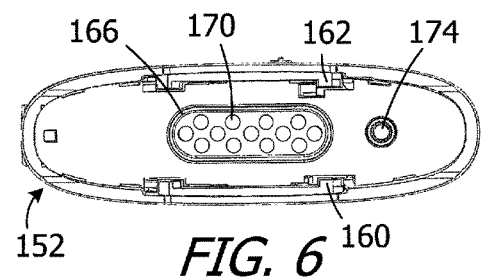
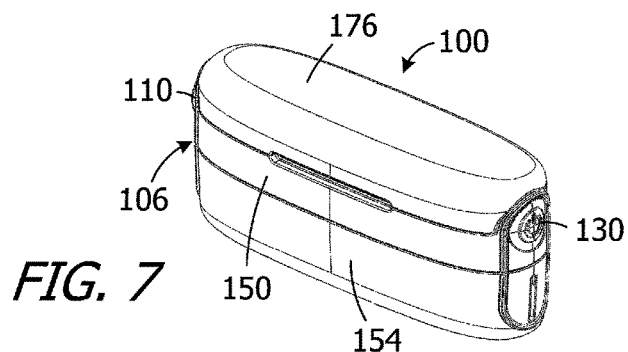

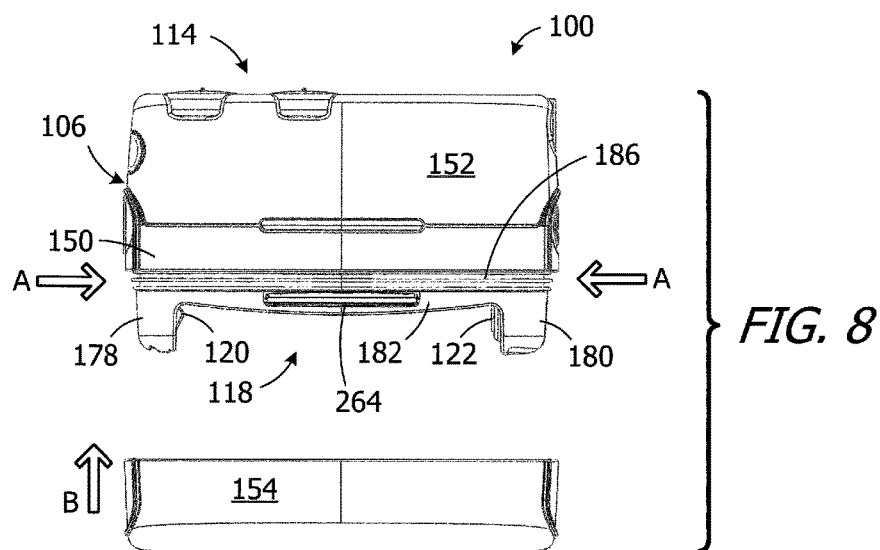
FIG. 8
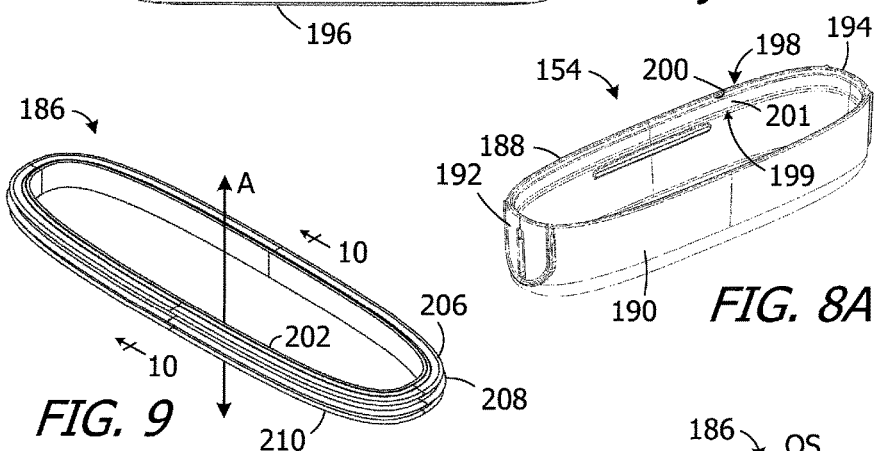
FIG. 8A
FIG. 9
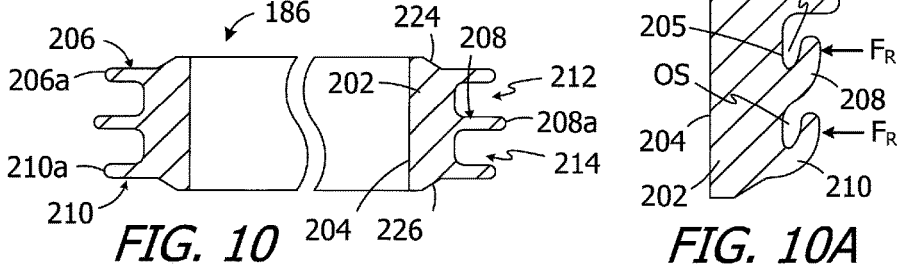
FIG. 10
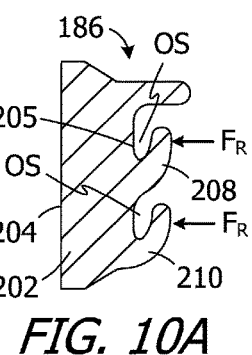
FIG. 10A

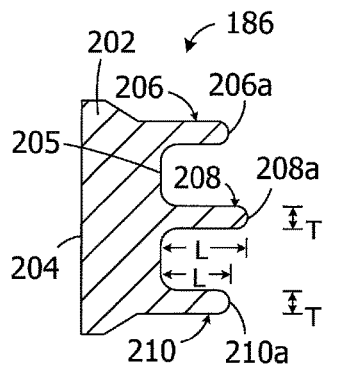
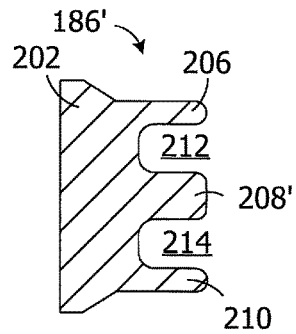
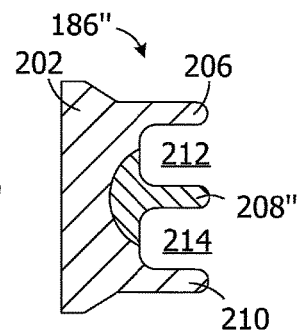
FIG. 15        FIG. 16A        FIG. 16B
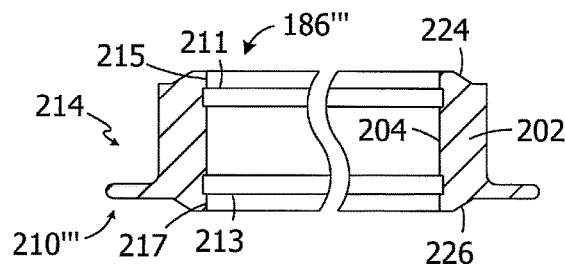
FIG. 16C
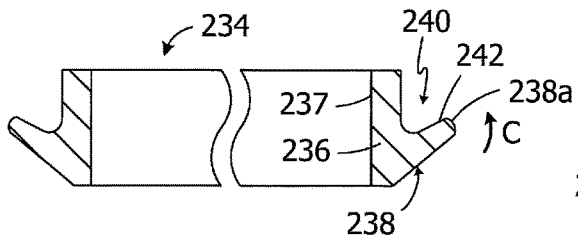
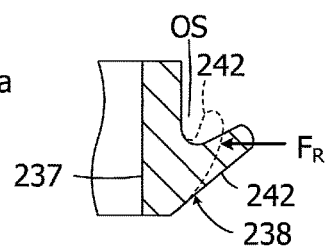
FIG. 17        FIG. 17A

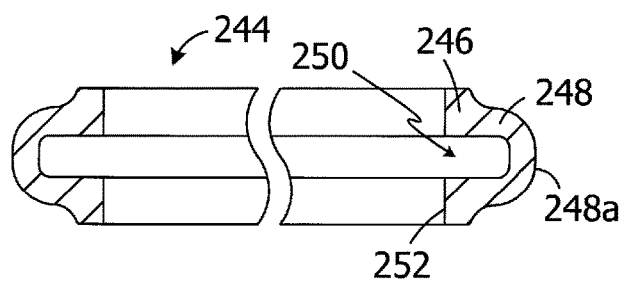
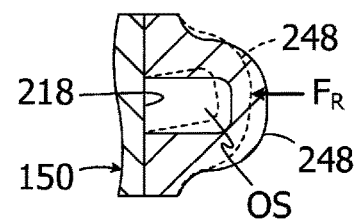
FIG. 18          FIG. 18A
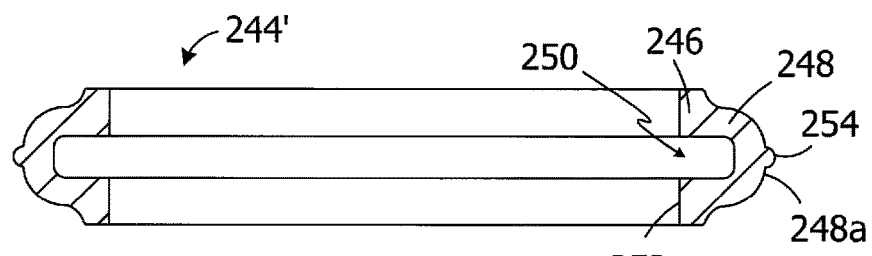
FIG. 19

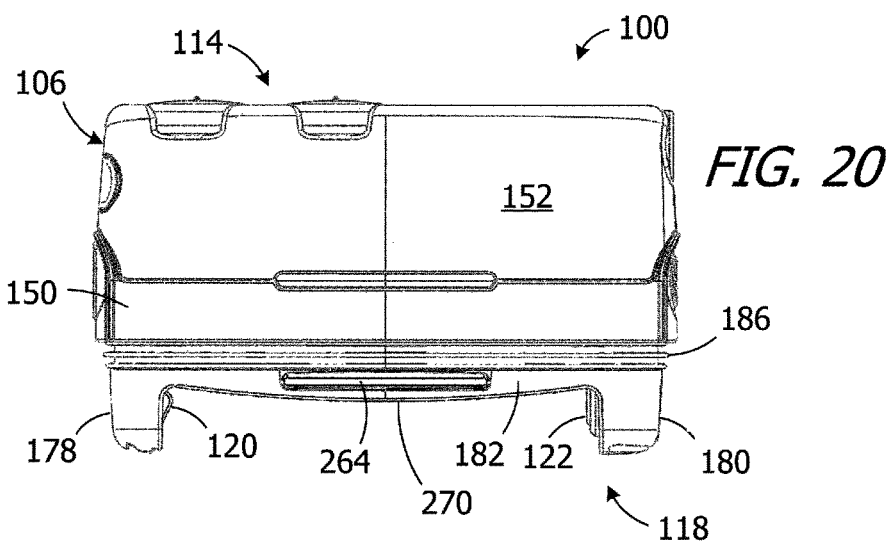
FIG. 20
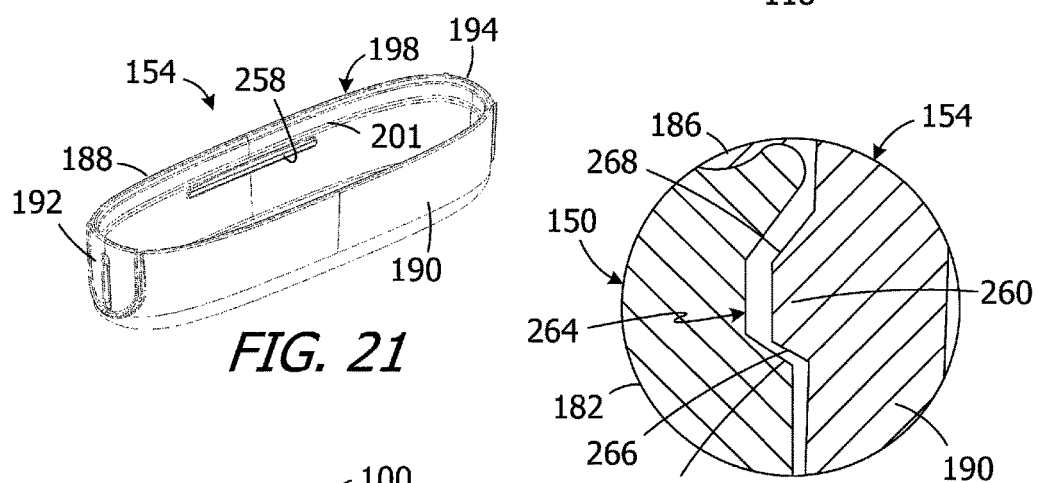
FIG. 21
FIG. 23
FIG. 22

SOUND PROCESSOR HOUSINGS, SOUND PROCESSORS AND IMPLANTABLE COCHLEAR STIMULATION SYSTEMS INCLUDING THE SAME

CROSS-REFERENCE TO RELATED APPLICATIONS

This application is the U.S. National Stage of PCT App. Ser. No. PCT/US2011/061563, filed Nov. 19, 2011, which claims priority U.S. Prov. App. Ser. No. 61/424,571, filed Dec. 17, 2010.

BACKGROUND

1. Field

The present disclosure relates generally to sound processors such as, for example, the sound processors in implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implantable device, a sound processor unit, and a microphone that is in communication with the sound processor unit. The implantable device communicates with the sound processor unit and, to that end, some ICS systems include a headpiece that is in communication with both the sound processor unit and the implantable device. In one type of ICS system, the sound processor unit is worn behind the ear (a "BTE unit"), while other types of ICS systems have a body worn sound processor unit (or "body worn unit"). The body worn unit, which is larger and heavier than a BTE unit, is typically worn on the user's belt or carried in the user's pocket. In those instances where body worn units have a replaceable battery, the body worn unit housing will have a battery compartment and a removable battery compartment cover. One example of a conventional body worn unit is the Advanced Bionics Platinum Series body worn unit.

Body worn units may be preferable to BTE units in a number of instances. For example, BTE units tend to be too big for infants, and toddlers tend to remove and/or damage BTE units. Body worn units, on the other hand, can be attached to a harness that positions the sound processor unit on the infant or toddler's back, where it is difficult for the infant or toddler to reach. Many adults prefer BTE units for most everyday activities, but prefer body worn units for sports and other activities.

The present inventor has determined that conventional body worn units are susceptible to improvement. For example, the present inventor has determined that the seals associated with battery compartment covers are susceptible to improvement. The present inventor has also determined that that it would be desirable to secure the battery compartment cover to the remainder of the body worn unit housing in a manner that it would reduce the likelihood that an infant or toddler could remove the cover without making it more difficult for adults to remove the cover.

SUMMARY

A sound processor housing in accordance with at least one of the present inventions includes a main portion with a power supply receptacle, a power supply receptacle cover, and a seal with a deflectable portion and a material-free region into which the deflectable portion deflects in response to the application of radial force. The present inventions also include sound processors with such a housing, and cochlear stimulation systems with a cochlear implant and a sound processor with such a housing.

A sound processor housing in accordance with at least one of the present inventions includes a main portion with a power supply receptacle, a power supply receptacle cover, a seal and means for creating an air gap between the housing and the portion of the seal to which the radial force is applied. The present inventions also include sound processors with such a housing, and cochlear stimulation systems with a cochlear implant and sound processors with such a housing.

Such housings, sound processors and systems are advantageous for a variety of reasons. For example, during the slide-on radial compression of seals associated with closing the present power supply receptacle covers, the present seals produce equal or better compartment sealing with less compressive force than would be realized with conventional solid o-ring seals.

A sound processor housing in accordance with at least one of the present inventions includes a main portion with a power supply receptacle, a power supply receptacle cover that has side walls that are substantially longer than the ends walls and the side walls are resiliently movable between a radially extended position and a radially retracted position, and a connector that secures a power supply receptacle cover side wall to the main portion.

A sound processor housing in accordance with at least one of the present inventions includes a main portion with a power supply receptacle, a power supply receptacle cover with side walls that are substantially longer than the ends walls, and a connector that secures the cover to the main portion. The power supply receptacle cover and connector are configured such that the connector is prevented from disconnecting when inward radial force is applied to the side walls of the power supply receptacle cover.

Such housings, sound processors and systems are advantageous for a variety of reasons. For example, the power supply receptacle covers in such housings are, as is described below, difficult for an infant or toddler to remove, yet not difficult for an adult to remove.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a functional block diagram of an ICS system in accordance with one embodiment of a present invention.

FIG. 2 is a perspective view of a sound processor in accordance with one embodiment of a present invention.

FIG. 3 is a perspective view of a sound processor in accordance with one embodiment of a present invention.

FIG. 4 is an exploded perspective view of a sound processor in accordance with one embodiment of a present invention.

FIG. 5 is a plan view of a portion of a sound processor in accordance with one embodiment of a present invention.

FIG. 6 is a plan view of a portion of a sound processor in accordance with one embodiment of a present invention.

FIG. 7 is a perspective view of a sound processor in accordance with one embodiment of a present invention.

FIG. 8 is an exploded side view of a sound processor in accordance with one embodiment of a present invention.

FIG. 8A is a perspective view of a power supply receptacle cover in accordance with one embodiment of a present invention.

FIG. 9 is a perspective view of a seal in accordance with one embodiment of a present invention.

FIG. 10 is a section view taken along line 10-10 in FIG. 9.

FIG. 10A is a section view showing a portion of seal illustrated in FIG. 10 in a radially compressed state.

FIG. 15 is a section view of a seal in accordance with one embodiment of a present invention.

FIG. 16A is a section view of a seal in accordance with one embodiment of a present invention.

FIG. 16B is a section view of a seal in accordance with one embodiment of a present invention.

FIG. 16C is a section view of a seal in accordance with one embodiment of a present invention.

FIG. 17 is a section view of a seal in accordance with one embodiment of a present invention.

FIG. 17A is a section view showing a portion of FIG. 17.

FIG. 18 is a section view of a seal in accordance with one embodiment of a present invention.

FIG. 18A is a section view showing a portion of FIG. 18.

FIG. 19 is a section view of a seal in accordance with one embodiment of a present invention.

FIG. 20 is a side view of a sound processor in accordance with one embodiment of a present invention with the power supply receptacle cover removed.

FIG. 21 is a perspective view of a power supply receptacle cover in accordance with one embodiment of a present invention.

FIG. 22 is a section view of a portion of a sound processor in accordance with one embodiment of a present invention with the power supply receptacle cover in place.

FIG. 23 is an enlarged view of a portion of FIG. 22.

DETAILED DESCRIPTION OF THE EXEMPLARY EMBODIMENTS

Figure 11:
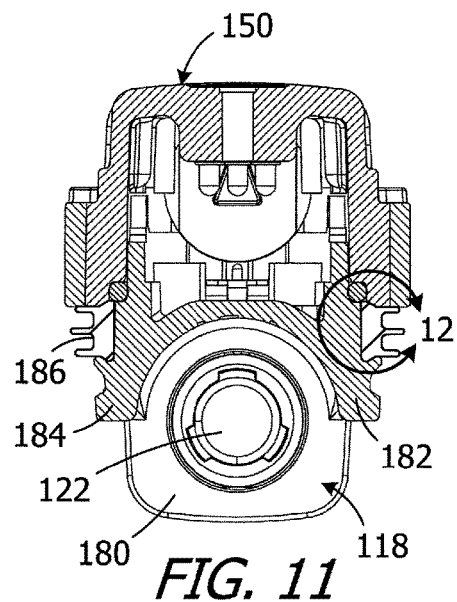
FIG. 11 is a section view of a portion of a sound processor in accordance with one embodiment of a present invention with the power supply receptacle cover removed.

The following is a detailed description of the best presently known modes of carrying out the inventions. This description is not to be taken in a limiting sense, but is made merely for the purpose of illustrating the general principles of the inventions.

The present inventions have application in a wide variety of systems that provide sound (i.e. either sound or a perception of sound) to the hearing impaired as well as others who require such systems on a situational basis. One example of such a system is an ICS system where an external sound processor communicates with a cochlear implant and, accordingly, the present inventions are discussed in the context of ICS systems. The present inventions are not, however, limited to ICS systems and may be used in combination with other systems for the hearing impaired that currently exist, or are yet to be developed.

One example of a body worn sound processor ("sound processor") is generally represented by reference numeral 100 in FIGS. 1-3. The exemplary sound processor 100, which may be combined with a headpiece 102 and a cochlear implant 104 to form an ICS system 10, includes a housing 106 in which and/or on which various components are supported. Such components may include, but are not limited to, sound processor circuitry 108, a headpiece port 110, an auxiliary device port 112 for an auxiliary device such as a mobile phone or a music player, a control panel 114, a Euro Plug receptacle 116 (for a Euro Plug such as that associated with the Phonak MLxi FM receiver), and a power supply receptacle 118 with electrical contacts 120 and 122 for a removable battery or other removable power supply 124 (e.g. rechargeable and disposable batteries or other electrochemical cells). Power supply receptacles are also sometimes referred to as "battery compartments" when they are intended for use with a battery. The headpiece port 110 and auxiliary device port 112 may be connected to the sound processor circuitry 108 by way of, for example, a signal splitter/combiner (not shown) such as that found in the Platinum Signal Processor body worn unit from Advanced Bionics Corporation. In the illustrated embodiment, the control panel 114 includes a volume knob 126 and a program switch 128. A power button 130 and a bayonet release button 132 are also carried on the housing 106. The bayonet release button 132 actuates a bayonet mechanism to release the housing control portion 152 from the housing main portion 150 (described below).

The headpiece 102 in the exemplary ICS system 10 includes a cable 134 which may be connected to the headpiece port 110, a microphone 136, an antenna 138 and a positioning magnet 140. The exemplary cochlear implant 104 includes an antenna 142, an internal processor 144, a cochlear lead 146 with an electrode array, and a positioning magnet (or magnetic material) 148. The transmitter 138 and receiver 142 communicate by way of electromagnetic induction, radio frequencies, or any other wireless communication technology. The positioning magnet 140 and positioning magnet (or magnetic material) 148 position the headpiece antenna 138 over the cochlear implant antenna 142. During use, the microphone 136 picks up sound from the environment and converts it into electrical impulses, and the sound processor 100 filters and manipulates the electrical impulses and sends the processed electrical signals through the cable 134 to the transmitter 138. Electrical impulses received from an auxiliary device are processed in essentially the same way. The receiver 142 receives signals from the transmitter 138 and sends the signals to the cochlear implant internal processor 144, which modifies the signals and passes them through the cochlear lead 146 to the electrode array. The electrode array may be wound through the cochlea and provides direct electrical stimulation to the auditory nerves inside the cochlea. This provides the user with sensory input that is a representation of external sound waves which were sensed by the microphone 136.

It should be noted that, in other implementations, communication between the sound processor and a headpiece and/or auxiliary device may be accomplished through wireless communication techniques. It should also be noted that, in other implementations, the sound processor may be configured to directly communicate with the cochlear implant (i.e. without a headpiece and associated cable).

The exemplary sound processor 100 may be carried by the user in a variety of ways. By way of example, but not limitation, the sound processor 100 may be carried in the user's pocket, secured to a belt with a belt clip that is either part of housing 106 or a separate carrier, or placed in a harness that is configured to be worn by a small child.

Referring more specifically to FIGS. 2 and 3, the exemplary housing 106 includes a main portion 150, a control portion 152 and a power supply receptacle cover ("PSR cover") 154 that may be detachably connected to the housing main portion 150 in the manner described below. The housing main portion 150 supports and/or houses the sound processor circuitry 108, headpiece port 110 and power button 130, and includes the power supply receptacle 118. The control portion 152 supports and/or houses the auxiliary device port 112, control panel 114, Euro Plug receptacle 116 and bayonet release button 132. In other words, in the exemplary implementation, the main portion 150 supports and/or houses those elements of the sound processor 100 that are required for the ICS system 10 to function, while the control portion 152 includes various elements that are only required from time to time (e.g. the volume knob 126) or are merely useful options (e.g. the auxiliary device port 112).

In the exemplary implementation, the sound processor 100 is configured such that the housing control portion 152 (and the functional elements associated therewith) may be mechanically and electrically separated from the housing main portion 150 (and the functional elements associated therewith) in the manner illustrated in FIG. 4. To that end, and referring also to FIGS. 5 and 6, the housing main portion 150 includes mechanical connectors 156 and 158 that are configured to mate with corresponding connectors 160 and 162 on the housing control portion 152. The housing main portion 150 and control portion 152 also include electrical connectors 164 and 166 with a plurality of contacts 168 and 170. An alignment locater feature, such as a post 172 and an opening 174 that receives the post and keys orientation, is also provided. Turning to FIG. 7, the sound processor 100 also includes a cover 176, with the same mechanical connectors (not shown) as the control portion 152, that may be used to protect the electrical connector 164 when the control portion is not in use.

It should also be noted here that, in other implementations, the sound processor may be configured such that the housing main portion and housing control portion define a single, integral unit that may not be separated in the manner described above.

As illustrated in FIG. 8, the power supply receptacle 118 in the exemplary embodiment is defined by various portions of the housing main portion 150. In particular, the housing main portion 150 has a pair of end walls 178 and 180 and a pair of side walls 182 and 184 (FIG. 11) that together define the volume, or at least a portion of the volume, in which a battery or other power supply is held. The electrical contacts 120 and 122 are carried on the end walls 178 and 180 and, in the exemplary embodiment, contact 120 is a resilient contact that is depressed as the battery or other power supply is positioned between the contacts. The resilient contact 120 presses against the battery or other power supply to hold it in place. The housing main portion 150 also has a connector 264, which is used to hold the PSR cover 154 in place as is discussed below with reference to FIGS. 20-27.

The exemplary sound processor 100 is also configured for use in or around water and, accordingly, is configured so as to insure that the power supply receptacle 118 is waterproof. More specifically, a seal 186 is carried on the housing main portion 150 in the manner illustrated in FIG. 8. Generally speaking, the exemplary seal 186 may be a resilient band that extends around the entire perimeter of the housing main portion 150 and contacts the entire perimeter of the inner surface of the PSR cover 154, i.e. without gaps or "uninterrupted," with a relatively constant force that is sufficient to prevent ingress of liquid. Although the seal 186 is removable and replaceable, it is held in the illustrated location during use. It should also be noted that the seal 186 is compressed radially when the PSR cover 154 is moved from the detached/open state (FIG. 8) where the power supply receptacle is accessible to the attached/covered state (FIGS. 2-3) where the power supply receptacle is not accessible. Put another way, the seal 186 is compressed in a direction that is perpendicular or at least substantially perpendicular (note arrows A) to the direction that the PSR cover 154 moves as it slides onto the housing main portion 150 and over the seal (note arrow B). The use of the phrase "radial compression" does not, however, impart a shape limitation on the housing and, in particular, does not require the housing to be circular or otherwise curved.

Radial compression of a seal differs from axial compression in that axial compression occurs when the seal is compressed in the same direction as, in the present context, a cover is moving. The present inventor has determined that slide-on axial compression of seals is less than optimal in the context of the present housing 106 because of the required constant force required to maintain seal compression and, accordingly, slide-on radial compression of the seal is employed in the illustrated embodiment. Solid (i.e. non-hollow) o-ring seals are frequently employed in slide-on axial compression applications such as plumbing fittings. The present inventor has, however, determined that there are a number of issues associated with conventional solid o-ring seals when they are used in a slide-on, radial compression environment. For example, solid o-ring seals require a relatively high amount of force for compression simply because they define a solid geometric shape, such as a circle, in cross-section. The cross-sectional area of an o-ring is generally unchanged when put under radial compression causing shape change. The required force to cause and maintain displacement of the o-ring shape is substantial and the resultant shape change must have adjacent open space to move into. As such, the distance that a solid o-ring seal can project outwardly into the path of the cover must be limited. Otherwise, it would be difficult to slide the cover onto the remainder of the housing. Portions of the housing could also yield under the relatively high forces, which creates in variations in the compression force, which could, in turn, result in open spots and leaks.

The exemplary seal 186 is configured to overcome the shortcomings associated with solid o-ring seals. In particular, as described below, the exemplary seal 186 has one or more portions that deflect and one or more open spaces (or "air gaps") into which the portions can deflect during radial compression. In other words, at least one portion of the seal compressed into an air gap that was not previously occupied by seal material. Conversely, when a seal has a solid cross-section (e.g. a solid circle), the seal material, under compression, will change shape only if the beam strength of confining adjacent structures are strong (stiff) enough to bear the radial load.

There are a variety of benefits associated with the use of such open spaces. For example, less force is required to radially compress the present seal a particular distance as compared to a seal that is solid in cross-section. Thus, a seal that is the same or better (e.g. without yield and variations in compression force) may be achieved while at the same time reducing the amount of force required to move the PSR cover 154 from the open state to the covered state.

In at least some implementations, the configuration of the PSR cover 154 is such that it facilitates the controlled radial compression of the seal 186. To that end, and referring to FIGS. 8 and 8A, the PSR cover 154 in the exemplary implementation includes side walls 188 and 190, end walls 192 and 194, a bottom wall 196 and an open end 198 opposite the bottom wall. The intersections of the side and end walls 188-194, and to some extent the side and end walls themselves, are curved. The cover walls in other implementations may define a rectangular shape with 90 degree corners. The exemplary PSR cover 154 also includes an inner surface 199, with a tapered transition portion 200 and a seal portion 201, that extends completely around the perimeter of the cover. The circumference of the inner surface 199 is greatest at the open end 198, then decreases through the transition portion 200 such that the slope is about 1.0 to about 1.7, and then is substantially constant in the seal portion 201. The transition portion 200 and seal portion 201 cooperate with the seal 186 in the manner described below with reference to FIGS. 13 and 14.

As illustrated in FIGS. 9 and 10, the exemplary seal 186 includes a base member 202, which defines the inner surface 204 of the seal, and a plurality of protrusions 206-210 that extend outwardly from the base member and have longitudinal ends 206a-210a. The seal 186 is formed from resilient material (discussed below) and, as is illustrated in FIG. 9, defines a closed geometric overall shape (e.g. circular or the illustrated oval) with an axis A. "Radial compression" is compression in a direction that is perpendicular to the axis A, "radial force" is force that is applied in a direction that is perpendicular to the axis A, and a "radial direction" is a direction that is perpendicular to the axis A. The seal 186 is slightly smaller than the portion of the housing main portion 150 on which is it is to be supported. As a result, the seal 186 will be pre-stressed when placed on the housing to prevent ingress of liquid between the seal inner surface 204 and the housing. The exemplary seal 186 also includes material-free regions 212 and 214 that are respectively located between protrusions 206 and 208 and protrusions 208 and 210. The material free regions 212 and 214 provide open spaces (or "air gaps") into which portions of the seal deflect during the slide-on radial compression that occurs when the PSR cover 154 is secured to the housing main portion 150.

To that end, FIG. 10A shows a cross-section taken in a plane that extends through the Axis A as a portion of the seal is exposed to radial force $F_R$ in the manner described below with reference to FIGS. 11-14. The radial force $F_R$ deflects the protrusions 208 and 210 into the material free regions 212 and 214 (FIG. 10). There are, at least during the radial compression, open spaces OS located between (in the radial direction) the points at which the radial force $F_R$ is being applied and the inner surface 204 of the seal 186 and/or the outer surface of the portion of the housing on which the seal is supported. The open spaces OS remain after the radial compression is complete in the illustrated implementation. The open spaces OS in the illustrated implementation are also located between (in the radial direction) the outer surface 205 of the seal base member 202 and the deflected protrusions 208 and 210. The deflected protrusions fold into available space providing outward radial loading which dynamically adjusts to fit into the available space. Conversely, if the seal were a solid circle or other geometric shape in cross-section, there would not be an open space between (in the radial direction) the point at which radial force is being applied and the inner surface of the seal. The solid circle would simply bulge axially in response to the radial force. When, as previously described, the seal has a solid cross-section (e.g. a solid circle), the seal material, under compression, will change shape only if the beam strength of confining adjacent structure is strong (stiff) enough to bear the radial load.

Although the protrusions 206-210 are generally planar structures that extend radially outwardly and are perpendicular to the base member inner surface 204 in the illustrated embodiment, other configurations may be employed. By way of example, but not limitation, other seals that have open spaces for radial compression are described below with reference to FIGS. 16A-19.

Figure 12:
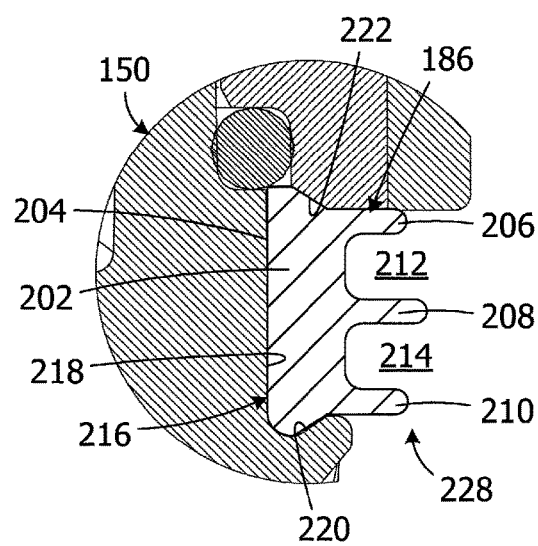
FIG. 12 is an enlarged view of a portion of FIG. 11.
Figure 13:
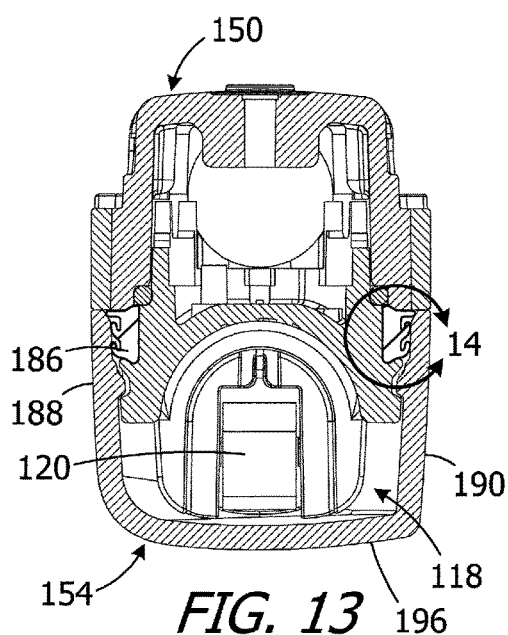
FIG. 13 is a section view of a portion of a sound processor in accordance with one embodiment of a present invention with the power supply receptacle cover in place.
Figure 14:
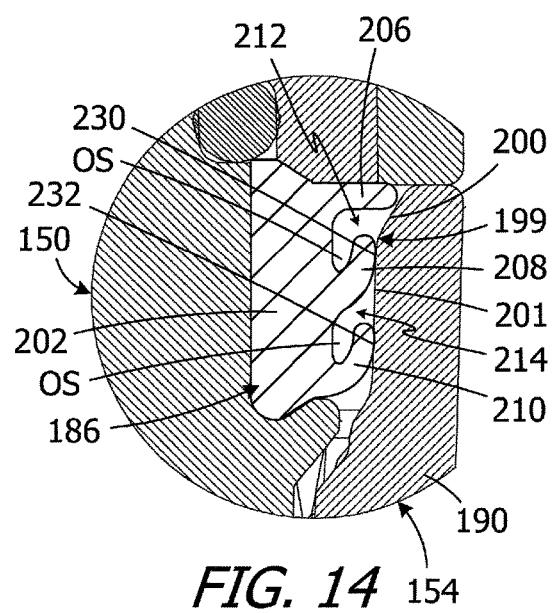
FIG. 14 is an enlarged view of a portion of FIG. 13.

Turning to FIGS. 11 and 12, the exemplary housing main portion 150 has a channel 216 into which the seal 186 may be inserted. The channel 216 has an inner surface 218 that abuts the seal inner surface 204. The channel 216 also has a pair of inwardly projecting surfaces 220 and 222. The seal main portion 202 has corresponding surfaces 224 and 226 (FIG. 10). The seal 186 is stretched and deflected into the channel 216 during assembly and held in the channel 216 by the inwardly projecting surfaces 220 and 222. So arranged, the protrusions 206-210 will extend radially outwardly from the main portion 202 and one or more of the protrusion will be located within a region 228 that will ultimately be occupied by a portion of the PSR cover 154. As the PSR cover 154 in the exemplary implementation moves through the region 228 (FIG. 12), the inner surface transition portion 200 will sequentially engage and deflect the protrusions 210 and 208. When the PSR cover 154 reaches attached/covered state, which is illustrated in FIGS. 13 and 14, the protrusions 208 and 210 will be deflected in the manner shown such that they engage the inner surface seal portion 201 at contact points 230 and 232 and there are open spaces OS between the protrusions and the main portion 202. Each contact point 230 and 232, which are the points at which the radial force $F_R$ (FIG. 10A) is applied to the seal 186, extends around the perimeter of the PSR cover 154 with enough force to prevent ingress of fluid.

It should be noted here that gradually deflecting the protrusions 208 and 210 with the transition portion 200 of the exemplary PSR cover inner surface 199, as opposed to the more abrupt deflection that would occur if the seal portion 201 extended all the way to the open end 198, provides a number of beneficial results. For example, the deflection of the protrusions 208 and 210 in the exemplary seal 186, as well as the deflection of various portions of the seals described below, occurs in a gradual manner. The protrusions 208 and 210 are deflected axially and radially by the transition portion 200 and then radially by the seal portion 201. As such, the radial force applied to the seal, as well as the axial resistance that the user experiences, increases in a gradual manner and the transition from the detached/open state to the attached/covered state is smooth.

Although the protrusions 206-210 may be identical in some implementations, the protrusion 208 in the exemplary seal 186 is configured so as to have different structural characteristics than the protrusions 206 and 210. The differences in structural characteristics are differences that result in differences in sealing characteristics generally, and the creation of more sealing force at protrusion 208 in particular. Referring to FIG. 15, in the exemplary seal 186, the length L of the protrusion 208 is greater than the length of protrusion 210, while the thicknesses T of protrusions 208 and 210 are same. Given the fact that the distance between the seal base member 202 and the seal portion 201 of the PSR cover inner surface 199 is essentially the same at each protrusion, and referring to FIG. 14, the protrusion 208 will undergo a greater degree of deflection and radial compression than the protrusion 210 because it is longer. As such, as despite the fact that the protrusions are the same thickness and formed from the same materials, the protrusion 208 will form a tighter seal than the protrusion 210 and will act as the primary portion of the seal. Locating the primary portion of the seal sufficiently away from the open end 198 is advantageous for insuring that the seal makes uniform radial contact with the PSR cover inner surface 199. The protrusion 210 functions as the secondary portion of the seal to prevent ingress of liquid should liquid pass the seal formed by protrusion 208. Such liquid will be at a lower pressure than liquid at the seal formed by protrusion 208.

It should be noted here that, given the respective dimensions of the protrusion 206 and the inner surface transition portion 200, the protrusion 206 does not create a seal or at least any substantial seal. The protrusion 206 may, therefore, be omitted in some embodiments. The protrusion 206, which is identical to protrusion 210, is included in the exemplary seal 186 for a number of other reasons. Most notably, the inclusion of the protrusion 206 makes the seal 186 symmetric about the protrusion 208 and, accordingly, it is reversible. If the seal 186 is mounted "upside down" on the housing 106, there will be no change in function and, in some instances, the life of the seal may be extended if it is removed and reversed after some period of use. The beam strength of the seal 186, as defined by the material thickness in the radial direction, is symmetric in the axial dimension. The additional beam strength associated with the protrusion 206 also improves the seal between the inner surface 204 and the inner surface 218 of the housing channel 216 created by the pre-stressing of the seal.

There are a variety of other ways to create protrusions with differing sealing characteristics. By way of example, but not limitation, differences in the respective thicknesses of the protrusions may be employed alone or in combination with differences in other structural characteristics (e.g. length) to create protrusions having the desired differences in sealing characteristics. The exemplary seal 186' illustrated in FIG. 16A, which is otherwise identical to seal 186, includes a protrusion 208' that is the same length as the protrusions 206 and 210 and is thicker than the protrusions 206 and 210. The exemplary seal 186" illustrated in FIG. 16B, which is otherwise identical to seal 186, includes a protrusion 208" that is the same length as the protrusions 206 and 210. Here, however, the protrusion 208" is formed from different, and stiffer, material. Such a seal may be manufactured by co-molding or other suitable process.

Figure 30:
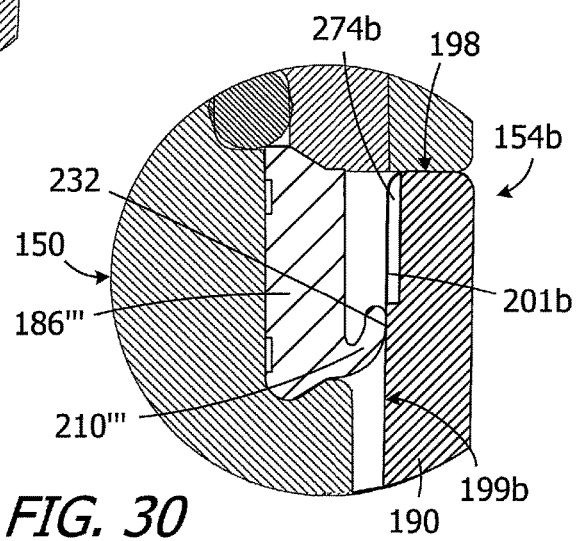
FIG. 30 is a section view of a portion of a sound processor main portion with the power supply receptacle cover in place.

The exemplary seal 186''' illustrated in FIG. 16C, which is otherwise identical to seal 186, includes only a single protrusion 210''', a single material free region 214, and one or more grooves, e.g. grooves 211 and 213, that are formed in the base member 202. The single protrusion 210''' forms a seal in the manner described above in the context of protrusion 208 (FIGS. 14-15) and, in the illustrated embodiment, the single protrusion is the same length as the protrusion 208. In embodiments that include the seal 186''', the inner surface of the associated PSR cover may include a tapered transition portion (e.g. transition portion 200 in FIG. 14), or as is illustrated in FIG. 30, the tapered transition portion may be omitted.

The grooves 211 and 213 are relatively shallow (e.g. about 0.004 inch), extend around the perimeter of the inner surface 204, and define relatively small (as compared to the entire surface 204) upper and lower contact surfaces 215 and 217 at the axial ends of the base member 202. The separate seals between the inner surface 204 and the inner surface 218 of the housing channel 216 formed at the spaced contact surfaces 215 and 217 are, in some instances, more readily controllable than a single seal formed from an inner surface without grooves. Although the exemplary grooves 211 and 213 are rectangular in shape, grooves of other shapes may be employed. It should also be noted that grooves, such as grooves 211 and 213, may be added to the inner surfaces of each of the other seal embodiments described above and below if so desired.

With respect to materials, suitable resilient materials for the exemplary seals disclosed herein include but are not limited to silicone. The dimensions of the seals will depend on the desired characteristics and the dimensions of the housing main portion and PSR cover, and the present seals are not limited to any particular dimensions unless such dimension are set forth in the claims below. Referring to FIG. 9, the unstretched major and minor dimensions (measured perpendicular to the Axis A) of the exemplary seal 186 are about 53.00 mm to 57.00 mm and about 14.00 mm to 16.00 mm. Referring to FIG. 15, the thickness of the base member 202, i.e. the distance between inner surface 204 and outer surface 205, is about 0.90 mm to 1.00 mm, the height of the base member is about 2.80 mm to 3.80 mm, the protrusions 206-210 are about 0.30 mm to 0.50 mm thick, the protrusions 206 and 210 are about 0.80 mm to 1.00 mm long, and the length of protrusion 208 is about 1.0 mm to 1.20 mm.

Seals that produce open spaces to facilitate radial compression are not limited to the configurations illustrated in FIGS. 15-16B. Other examples of seals with material-free regions that create open spaces (or "air gaps") for radial compression are illustrated in FIGS. 17-19. Such seals may be substituted for the seal 186 in the exemplary sound processor 100.

The exemplary seal 234 illustrated in FIG. 17 includes a base member 236 and a single protrusion 238, with a longitudinal end 238a, that extends outwardly from the base member in a direction that has a radial component and an axial component. The seal 234 is formed from resilient material (discussed above) and defines an overall closed geometric shape about its axis (e.g. circular or oval, as shown in FIG. 9). The seal 234 is slightly smaller than the portion of the housing main portion 150 on which is it is supported. Thus, the seal 234 will be pre-stressed when placed on the housing to prevent ingress of liquid between the seal inner surface 237 and the housing. The exemplary seal 234 also includes a material-free region 240. The protrusion 238, which is not perpendicular the base member 236, extends upwardly (in the illustrated orientation) such that an acute angle is defined between the protrusion and the base member. During the slide-on radial compression of the seal 234 that occurs when the PSR cover 154 is being secured to the housing main portion 150 (note arrow B in FIG. 8; and note FIG. 14), the transition portion 200 of the cover inner surface 199 will engage the longitudinal end 238a and cause the protrusion 238 to pivot in the manner represented by arrow C.

Once the PSR cover 154 is secured to the housing main portion 150, the protrusion surface 242 will press against the seal portion 201 around the perimeter of the cover with enough force to preventingress of liquid. The deflection of the protrusion 238 is shown in dashed lines in FIG. 17A. An open space OS will be located between (in the radial direction) the point at which the radial force $F_R$ is being applied and the seal inner surface 237. As noted above, the open space OS provides room for the seal configuration to fold into with minimal compressive loading. When, as previously described, the seal has a solid cross-section (e.g. a solid circle), the seal material, under compression, will change shape only if the beam strength of confining adjacent structure is strong (or "stiff") enough to bear the radial load. Conversely, the protrusion 238 folds into available space providing outward radial loading which dynamically adjusts to fit into the available space. A solid circle would simply bulge axially in response to the radial force.

The exemplary seal 244 illustrated in FIG. 18 includes a base member 246 and a single protrusion 248, with a longitudinal end 248a, that extends outwardly from the base member. The seal 244 is formed from resilient material (discussed above) and defines an overall closed geometric shape about its axis (e.g. circular or oval, as shown in FIG. 9). The seal 244 is slightly smaller than the portion of the housing main portion 150 on which is it is supported so that the seal will be pre-stressed. The exemplary seal 244 also includes a material-free region 250 that extends around the perimeter of the seal. The material-free region 250 extends through the base member 246, which creates a discontinuity in the inner surface 252, and into the protrusion 248.

Once the PSR cover 154 is secured to the housing main portion 150, the protrusion 248 will press against the seal portion 201 around the perimeter of the cover with enough force to preventingress of liquid. The deflection of the protrusion 248 is shown in dashed lines in FIG. 18A. An open space OS will be located between (in the radial direction) the point at which the radial force $F_R$ is being applied and the housing channel inner surface 218. As noted above, the open space OS provides room for the seal configuration to fold into with minimal compressive loading. When, as previously described, the seal has a solid cross-section (e.g. a solid circle), the seal material, under compression, will change shape only if the beam strength of confining adjacent structure is strong (or "stiff") enough to bear the radial load. Conversely, the protrusion 248 folds into available space providing outward radial loading which dynamically adjusts to fit into the available space. A solid circle would simply bulge axially in response to the radial force.

The exemplary seal 244' illustrated in FIG. 19 is essentially identical to the seal 244 shown in FIG. 18, and similar elements are represented by similar reference numerals. Here, however, the longitudinal end 248a includes a protrusion 254 which provides a specific radial seal line of contact.

The PSR cover and seal arrangements described above are such that the waterproof rating at the PSR cover will be IPX7, i.e. there will be no ingress of visible water into the power supply receptacle 118 when the sound processor 100 is immersed in water at a depth of 1 meter for 30 minutes.

The exemplary sound processor 100 also includes a connector apparatus that secures the PSR cover 154 to the housing main portion 150. One example of such a connector apparatus is illustrated in FIGS. 20-23. Additionally, and as discussed in greater detail below with reference to FIGS. 24-27, the sound processor 100 is configured so as to insure that the PSR cover 154 must be gripped in a particular way to facilitate removal.

As illustrated for example in FIGS. 20-23, the exemplary connector apparatus 256 (FIG. 22) includes protrusions 258 and 260, which are carried by the PSR cover walls 188 and 190, and are configured to mate with indentations 262 and 264 in the side walls 182 and 184 of housing main portion 150. Each of the protrusions 258 and 260 includes two cam surfaces 266 and 268 (FIG. 23), and each of the side walls 182 and 184 includes edges 270 and 272 (FIGS. 22-23). The resilience of the PSR cover 154 allows the side walls 188 and 190 to deflect as the cover moves from the detached/open state (FIGS. 20 and 21) to the attached/covered state (FIGS. 22 and 23) and from the attached/covered state to the detached/open state. More specifically, as the PSR cover 154 moves from the detached/open state toward the housing main portion 150 (note arrow B in FIG. 8), the cam surfaces 268 on the cover protrusions 258 and 260 will engage the edges 270 of housing walls 182 and 184. As the PSR cover 154 continues to move in this direction, the cover walls 188 and 190 will deflect radially outwardly, as permitted by the resilience of the PSR cover 154, while the protrusions 258 and 260 pass the edges 270. The PSR cover walls 188 and 190 will remain deflected radially outwardly until the protrusions 258 and 260 are aligned with the indentations 262 and 264. At this point, the resilience of the PSR cover 154 will cause the walls 188 and 190 to move radially inwardly such that the protrusions 258 and 260 are located within the indentations 262 and 264, in their radially retracted positions, thereby locking the cover in place. Conversely, when the PSR cover 154 pulled in the opposite direction, the cam surfaces 266 on the protrusions 258 and 260 will engage the edges 272 of the side walls 182 and 184. The cover walls 188 and 190 will deflect radially outwardly, to their radially extended positions, and the protrusions 258 and 260 will move out of the indentations 262 and 264 as the PSR cover 154 continues to be pulled away from the housing main portions 150.

The protrusions 258 and 260 and indentations 262 and 264 in the illustrated embodiment are also elongate and located at the longitudinally central region of the housing side walls 182 and 184 and PSR cover side walls 188 and

190. The longitudinally central region of the PSR cover side walls 188 and 190 is the region of maximum radial extension.

Suitable resilient materials for the PSR cover 154 include, but are not limited to, a polycarbonate (PC)/acrylonitrile butadiene styrene (ABS) resin. Such materials, in combination with a wall thickness of about 0.050 inch and the other dimension of the cover described herein will allow the PSR cover 154 to resiliently deflect in the manner described above.

The main portion 150 and control portion 152 of the exemplary housing 106 may be formed from materials including, but not limited to, PCs, ABSs, PC/ABS blends, nylon and various combinations thereof. One specific example is Lexan® Resin HP1R, from SABIC Innovative Plastics Company. Another specific example is Noryl® PPO, a modified polyphenylene oxide. In one exemplary implementation, the main portion 150 may include a main structure formed from Lexan® Resin HP1R and a decorative overmold formed from a platable grade of PC/ABS with a chrome plating on the PC/ABS. In other implementations, the housing main portion 150 and control portion 152 may be formed from the same materials as the PSR cover 154, but will be stiffer due to the geometry.

It should be emphasized here that the connector apparatus 256 is merely one example of an apparatus that may be carried on the cover side walls 188 and/or 190 and used to secure the PSR cover 154 to the housing main portion 150. By way of example, but not limitation, an alternative PSR cover and housing main portion arrangement may be configured such that the locations of the above-described protrusions, indentations, cam surfaces and edges are reversed. Another alternative is to simply include a protrusion and indentation, along with the associated cam surfaces and edges, on one of the cover side walls 188 and 190. A connector apparatus similar to connector apparatus 256 may also be associated with the portion of the housing above (in the illustrated orientation) the seal and with the open end of the PSR cover, i.e. located on the other side of the seal. The protrusions and indentations may also have curved surfaces instead of the linear surfaces illustrated in, for example, FIG. 25.

The overall configuration of the housing 106 is such that the PSR cover 154 is a child resistant cover. In particular, the dimensions of the housing 106 and the location of the connector apparatus (e.g. the protrusions 258 and 260 and the indentations 262 and 264) make it exceedingly difficult for a young child (e.g. infants and toddlers up to about 4 years of age) to remove the PSR cover 154.

Referring to FIGS. 24-27, in the illustrated embodiment, the length L of the housing 106 is substantially greater than, e.g. at least about two times and in some instances at least about three times, the width W of the housing. The length L of the exemplary housing 106 is also relatively large. The "length" is the major dimension perpendicular to the axis A which, in the illustrated embodiment, is also perpendicular to direction of cover movement (note arrows E in FIG. 24). As used herein, "relatively large" means at least 2 inches, which is a length that a young child would find difficult to grip with sufficient force to remove the PSR cover 154. Exemplary values of the length L range from about 2 inches to about 4 inches, depending on the age of the child, and the illustrated embodiment is 2.3 inches long. The width W of the exemplary housing 106 is relatively small. The "width" is the minor dimension perpendicular to the axis A which, in the illustrated embodiment, is also to the direction of cover movement (note arrows E in FIG. 24). As used herein, "relatively small" means no more than 2 inches (e.g. when the length is 4 inches). Exemplary values of the width W range from about 0.25 inch to about 2 inches, and the illustrated embodiment is about 0.7 inches wide. The lengths of the housing main portion side walls 182 and 184 and the PSR cover side walls 188 and 190 closely correspond to, or are the same as, the length L of the housing 106, while the lengths of the housing main portion end walls 178 and 180 and the PSR cover end walls 192 and 194 closely correspond to, or are the same as, the width W of the housing 106. As noted above, the wall thickness of the PSR cover 154, in combination with the resiliency of the cover materials, facilitates the resilient radial deflection of the side walls 188 and 190.

Figure 24:
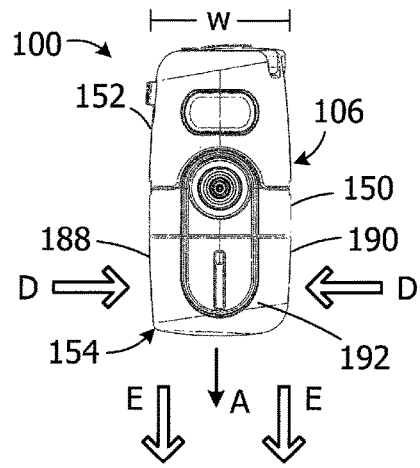
FIG. 24 is an end view of a sound processor in accordance with one embodiment of a present invention.
Figure 25:
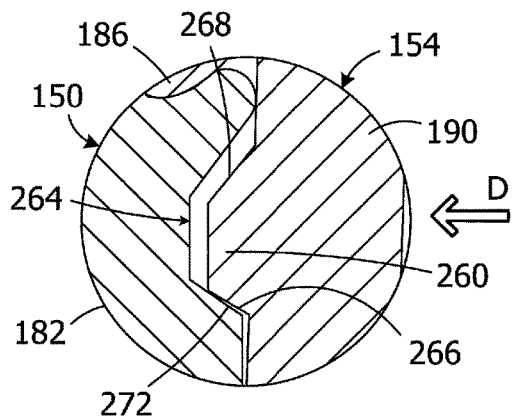
FIG. 25 is a section view of a portion of the sound processor illustrated in FIG. 24.
Figure 26:
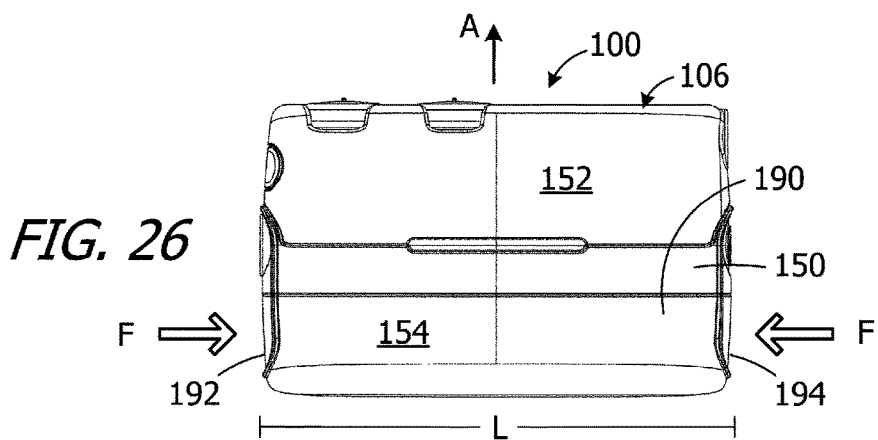
FIG. 26 is a side view of a sound processor in accordance with one embodiment of a present invention.

Given the configuration described in the preceding paragraph, its would be extremely difficult, as well as counter-intuitive, for a young child to grip the PSR cover at the end walls 178 and 180. The distance between the end walls 178 and 180 is too great to fit within a young child's hand. Instead, when attempting to pull the PSR cover 154 from the housing main portion 150, a young child will grip the PSR cover 154 at the side walls 188 and 190. The distance between side walls 188 and 190 is considerably smaller and, accordingly, they are easier to grip. A gripping force in the direction of arrows D will be applied to the side walls 188 and 190 when applying removal force in the direction of arrows E (FIG. 24). Applying gripping force in the direction of arrows D will, however, prevent the protrusions 258 and 260, which are carried by the PSR cover side walls 188 and 190 (FIG. 22), from moving out of the indentations 262 and 264. The gripping force prevents the PSR cover side walls 188 and 190 from moving radially outwardly. As the young child pulls harder in the direction of arrows E, he/she will also apply more force in the direction of arrows D to maintain a grip on the cover 154, thereby preventing the protrusions 258 and 260 from coming out of the indentations 262 and 264 despite the increase in the pulling force that would otherwise deflect the side walls 188 and 190 radially outwardly.

Figure 27:
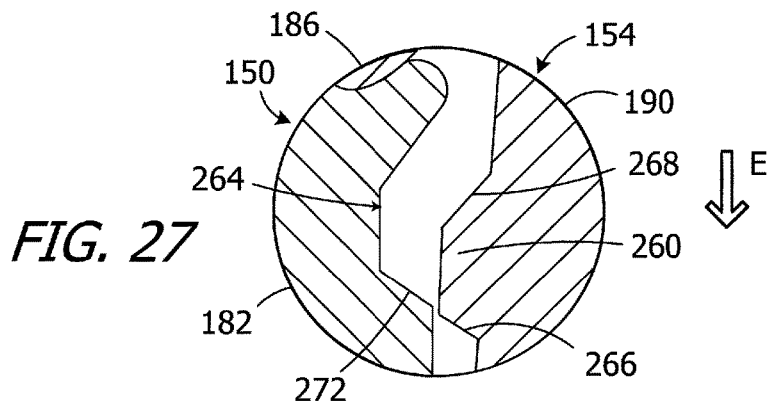
FIG. 27 is a section view of a portion of the sound processor illustrated in FIG. 26 after slight movement from the location illustrated in FIG. 26.

When an adult who is aware of the present configuration desires to remove the PSR cover 154 from the housing main portion 150, he/she will grip the cover at the end walls 178 and 180 and apply a gripping force in the direction of arrow F (FIG. 26) and removal force in the direction of arrows E (FIGS. 24 and 27). The cam surfaces 266 on the protrusions 258 and 260 will engage the edges 272 of the side walls 182 and 184 as the cover 154 moves in the direction of arrows E. Because there is no gripping force preventing the cover walls 188 and 190 from deflecting radially outwardly, the protrusions 258 and 260 will move out of the indentations 262 and 264 as the PSR cover 154 in the direction of arrows E, thereby unlocking the cover and permitting removal.

PSR covers may also be provided with structures that facilitate movement of the PSR cover to and from the attached/covered state (FIG. 22). More specifically, the robust seal provided by the seal 186 (or 186') may trap air within the power supply receptacle 118 as the PSR cover 154 approaches the attached/covered state during placement of the PSR cover over the power supply receptacle. The pressure of the air (if trapped) will then increase as the PSR cover 154 continues its movement to the attached/covered state, thereby creating a force that opposes the force being applied by the user. Similarly, when the user pulls the PSR cover 154 from the attached/covered state at the outset of the removal process, a suction force that is created by the trapped air will oppose removal of the PSR cover until the PSR cover has moved a distance sufficient to break the seal.

Figure 28:
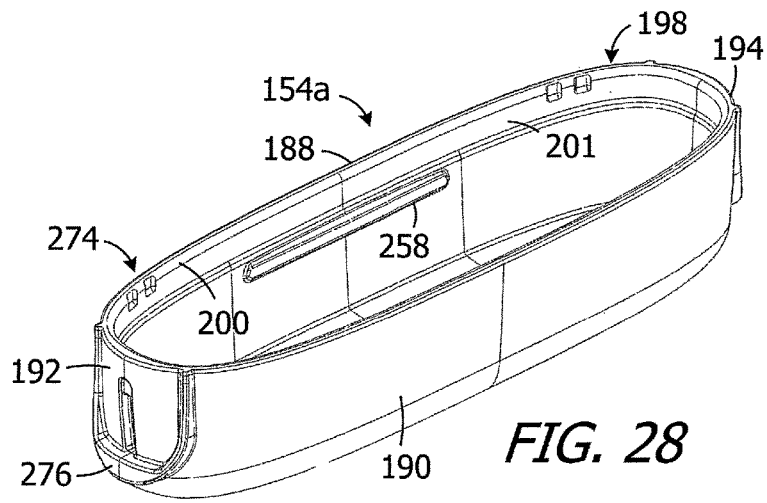
FIG. 28 is a perspective view of a power supply receptacle cover in accordance with one embodiment of a present invention.
Figure 29:
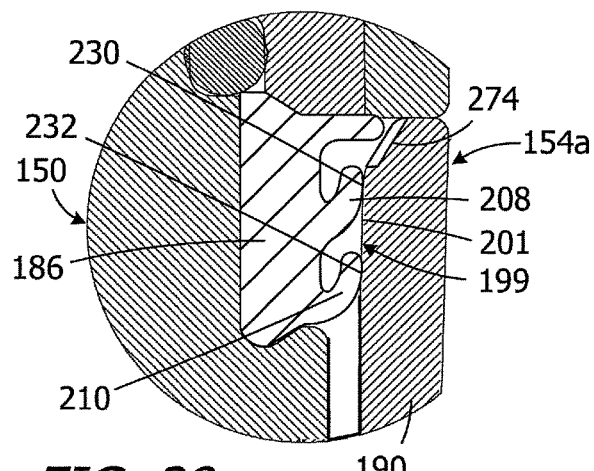
FIG. 29 is a section view of a portion of a sound processor main portion with the power supply receptacle cover illustrated in FIG. 28 in place.

One example of a PSR cover that is configured to vent air without effecting the seal provided by seal 186, and which may be incorporated into any of the sound processors described herein, is generally represented by reference numeral 154a in FIGS. 28 and 29. PSR cover 154a is essentially identical to PSR cover 154 and similar elements are represented by similar reference numerals. The PSR cover 154a also includes one or more vents. The vents may be of any suitable number, form or location. There are four sets of two vents 274 in the illustrated embodiment, with two sets on each side wall 188 and 190. The sets of vents 274 may be located at the same locations on the side walls 188 and 190, as they are in the exemplary embodiment, or may be at different locations.

In the illustrated embodiment, the vents 274 are located in the tapered transition portion 252 and, accordingly, do not effect the seal formed between the cover inner surface seal portion 201 and the seal protrusion 208 (FIG. 29) at contact point 230. However, during placement of the PSR cover 154a onto the housing main portion 150, the vents 274 permit air passage past the seal protrusion 208 and prevent the aforementioned pressure increase within the power supply receptacle 118. Similarly, after the PSR cover 154a has been moved a small distance from the attached/covered state during cover removal, the vents 274 will be aligned with the seal protrusion 208 so that air can be drawn into the power supply receptacle 118, thereby preventing the creation of suction force.

It should also be noted that the vents 274 are located near both longitudinal ends of each of the cover side walls 188 and 190 in the illustrated embodiment. Thus, should the PSR cover 154a be tilted relative to housing main portion 150 when the being placed on the main portion, i.e. should one of the end walls 192 and 194 be closer to the main portion than the other, venting will occur at the trailing vents 274 as the PSR cover straightens out prior to reaching the attached/covered state. Similarly, venting will occur if the user pulls from one end of the PSR cover 154a during removal. Venting will occur at all vents 274 during placement and removal when the PSR cover 154a is not tilted relative to the housing main portion 150.

The exemplary cover 154b illustrated in FIG. 30 is essentially identical to PSR cover 154a and similar elements are represented by similar reference numerals. Here, however, the cover 154b is configured for use with seal 186'''. To that end, the cover includes an inner surface 199b without a tapered transition portion. The seal portion 201b extends essentially to the open end 198. The single protrusion 210' protrusion 210''' forms a seal at contact point 232.

To facilitate movement of the PSR cover 154b to and from the attached/covered state, the PSR cover also includes vents 274b that may be of any suitable number, form or location. There may be four sets of two vents 274b, as is described above with reference to vents 274, with the vents being long enough to extend from about the open end 198 to the illustrated location adjacent to the contact point 232.

The exemplary PSR cover 154a illustrated in FIGS. 28 and 29 also includes a protrusion 276 on the cover end walls 192 and 194. The protrusions 276, which help the user grip the end walls 192 and 194, may also be employed on the PSR covers 154 and 154b.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A sound processor for use with a cochlear implant, the sound processor comprising:
   a housing including
      a main portion including a power supply receptacle,
      a seal, defining a closed geometric shape with an axis, carried by the housing main portion, and
      a power supply receptacle cover movable in the axial direction between an open state where the power supply receptacle is accessible and a closed state where the power supply receptacle is not accessible,
      the main portion, seal and power supply receptacle cover being respectively configured and arranged such that movement of the power supply receptacle cover from the open state to the closed state results in a radial force being applied to the seal by the power supply receptacle cover,
      the seal including a deflectable portion and defining a material-free region into which the deflectable portion deflects in response to the application of radial force by the power supply receptacle cover;
   sound processor circuitry carried within the housing; and
   a communication device adapted to operably connect the sound processor circuitry to the cochlear implant.

2. A sound processor as claimed in claim 1, wherein the seal includes a base member and the deflectable portion comprises a protrusion extending outwardly from the base member.

3. A sound processor as claimed in claim 2, wherein the protrusion extends radially outwardly from the base member.

4. A sound processor as claimed in claim 1, wherein the seal include a base member and the deflectable portion comprises first and second protrusions extending outwardly from the base member.

5. A sound processor as claimed in claim 4, wherein the first and second protrusions define different configurations.

6. A sound processor as claimed in claim 5, wherein the first and second protrusions define different lengths in the radial direction.

7. A sound processor as claimed in claim 5, wherein
   the seal includes a third protrusion with the same configuration as the second protrusion;
   the first protrusion is located between the second and third protrusions; and
   the seal is axially symmetric about the first protrusion.

8. A sound processor as claimed in claim 7, wherein the seal and power supply receptacle cover are respectively configured and arranged such that the first and second protrusions will be radially compressed when the power supply receptacle cover is in the closed state and the third protrusion will not be substantially radially compressed when the power supply receptacle cover is in the closed state.

9. A sound processor as claimed in claim 1, wherein the seal and power supply receptacle cover are respectively configured and arranged such that an air gap is located between, and is radially aligned with, the housing main portion and the portion of the power supply receptacle cover that applies radial compression force to the seal when the power supply receptacle cover is in the closed state.

10. A sound processor as claimed in claim 1, wherein the housing main portion and the power supply receptacle cover include respective portions of a latch that secures the power supply receptacle cover to the housing main portion.

11. A sound processor as claimed in claim 1, wherein
the power supply receptacle cover defines an open end, a closed end, and an inner surface; and
the inner surface includes a seal portion and a transition portion located between the seal portion and the open end.

12. A sound processor as claimed in claim 1, wherein the housing main portion, seal and power supply receptacle cover are configured such that there will be no ingress of visible water into the power supply receptacle when the sound processor is immersed in water at a depth of 1 meter for 30 minutes.

13. A sound processor as claimed in claim 1, wherein
the power supply receptacle cover defines an open end, a closed end, and an inner surface; and
the inner surface includes a seal contact point that is in contact with the deflectable portion when the power supply receptacle is in the closed state and at least one vent located between the seal contact point and the open end.

14. A sound processor as claimed in claim 1, wherein the communication device comprises a headpiece.

15. A sound processor for use with a cochlear implant, the sound processor comprising:
a housing including
a main portion including a power supply receptacle,
a seal defining a closed geometric shape with an axis, and including a deflectable portion, and carried on a surface of the housing main portion,
a power supply receptacle cover movable in the axial direction between an open state where the power supply receptacle is accessible and a closed state where the power supply receptacle is not accessible, the main portion, seal and power supply receptacle cover being respectively configured and arranged such that movement of the power supply receptacle cover from the open state to the closed state results in the cover applying a radial force to a portion of the seal, and
means for creating an air gap between the surface of the housing main portion on which the seal is carried and the portion of the seal to which the radial force is applied;
sound processor circuitry carried within the housing; and
a communication device adapted to operably connect the sound processor circuitry to the cochlear implant.

16. A sound processor as claimed in claim 15, wherein
the seal defines a perimeter that extends around the axis; and
the cover applies an uninterrupted radial force to a portion of the seal that extends completely around the perimeter of the seal.

17. A sound processor as claimed in claim 16, wherein the air gap and the portion of the seal to which the radial force is applied are aligned in the radial direction.

18. A sound processor as claimed in claim 15, wherein the air gap and the portion of the seal to which the radial force is applied are aligned in the radial direction.

19. A sound processor as claimed in claim 15, wherein the seal includes a base member and the deflectable portion comprises a protrusion extending outwardly from the base member.

20. A sound processor as claimed in claim 19, wherein the protrusion extends radially outwardly from the base member.

21. A sound processor as claimed in claim 15, wherein the seal include a base member and the deflectable portion comprises first and second protrusions extending outwardly from the base member.

22. A sound processor as claimed in claim 21, wherein the first and second protrusions define different configurations.

23. A sound processor as claimed in claim 22, wherein the first and second protrusions define different lengths in the radial direction.

24. A sound processor as claimed in claim 22, wherein
the seal includes a third protrusion with the same configuration as the second protrusion;
the first protrusion is located between the second and third protrusions; and
the seal is axially symmetric about the first protrusion.

25. A sound processor as claimed in claim 24, wherein the seal and power supply receptacle cover are respectively configured and arranged such that the first and second protrusions will be radially compressed when the power supply receptacle cover is in the closed state and the third protrusion will not be substantially radially compressed when the power supply receptacle cover is in the closed state.

26. A sound processor as claimed in claim 15, wherein
the power supply receptacle cover defines an open end, a closed end, and an inner surface; and
the inner surface includes a seal portion and a transition portion located between the seal portion and the open end.

27. A sound processor as claimed in claim 15, wherein the housing main portion and the power supply receptacle cover include respective portions of a latch that secures the power supply receptacle cover to the housing main portion.

28. A sound processor as claimed in claim 15, wherein the housing main portion, seal and power supply receptacle cover are configured such that there will be no ingress of visible water into the power supply receptacle when the sound processor is immersed in water at a depth of 1 meter for 30 minutes.

29. A sound processor as claimed in claim 15, wherein
the power supply receptacle cover defines an open end, a closed end, and an inner surface; and
the inner surface includes a seal contact point that is in contact with the deflectable portion when the power supply receptacle is in the closed state and at least one vent located between the seal contact point and the open end.

30. A sound processor as claimed in claim 15, wherein the communication device comprises a headpiece.

* * * * *